(12) United States Patent
Parrino et al.

(10) Patent No.: US 7,469,716 B2
(45) Date of Patent: Dec. 30, 2008

(54) MULTIWAY VALVE

(75) Inventors: Andrea Parrino, Mirandola (IT); Cesare Bulgarelli, San Possidonio (IT)

(73) Assignee: Gambro Lundia AB (SE)

( * ) Notice: Subject to any disclaimer, the term of this patent is extended or adjusted under 35 U.S.C. 154(b) by 672 days.

(21) Appl. No.: 10/525,728

(22) PCT Filed: Aug. 5, 2003

(86) PCT No.: PCT/IE03/03166

§ 371 (c)(1), (2), (4) Date: Feb. 25, 2005

(87) PCT Pub. No.: WO2004/022151

PCT Pub. Date: Mar. 18, 2004

(65) Prior Publication Data
US 2006/0005886 A1    Jan. 12, 2006

(30) Foreign Application Priority Data
Sep. 6, 2002    (IT)    .......................... MI2002A1895

(51) Int. Cl.
*F16K 37/00*    (2006.01)
*F16K 11/074*    (2006.01)
(52) U.S. Cl. .................... 137/556; 137/625.46; 137/559
(58) Field of Classification Search ................. 137/556, 137/553, 625.19, 625.46, 625.47, 559
See application file for complete search history.

(56) References Cited

U.S. PATENT DOCUMENTS

| | | | |
|---|---|---|---|
| 3,115,896 A | * | 12/1963 | Roberts et al. ......... 137/625.41 |
| 3,238,968 A | * | 3/1966 | Pecis ........................... 137/556 |
| 3,783,900 A | | 1/1974 | Waldbillig |
| 3,834,372 A | | 9/1974 | Turney |
| 3,921,955 A | * | 11/1975 | Haddad, Jr. ................. 251/297 |
| 4,085,046 A | | 4/1978 | Saporito, Jr. |
| 4,096,859 A | | 6/1978 | Agarwal et al. |
| 4,197,876 A | | 4/1980 | Lobdell |

(Continued)

FOREIGN PATENT DOCUMENTS

DE    297 15 833 U1    2/1998

(Continued)

OTHER PUBLICATIONS

International Search Report of International Application No. PCT/IB03/03166.

*Primary Examiner*—Stephen M Hepperle
*Assistant Examiner*—Andrew J Rost
(74) *Attorney, Agent, or Firm*—Finnegan, Henderson, Farabow, Garrett & Dunner L.L.P.

(57) ABSTRACT

What is provided is a flow shut-off element, particularly for use in the medical field of peritoneal dialysis, consisting of a valve body (2) having an inner cavity (3) and a plurality of accesses (4, 5, 6); a selector having a projecting portion inserted into the inner cavity of the valve body and movable relatively to the latter into a predetermined number of operating positions to create predetermined paths in which the fluid flow is permitted and/or shut off between the said accesses. Also provided is an auxiliary element interposed in a removable way between the valve body and the selector, this element having positioning means to enable an operator to determine when one of the said predetermined operating positions of the selector has been reached.

19 Claims, 6 Drawing Sheets

U.S. PATENT DOCUMENTS

| | | |
|---|---|---|
| 4,207,923 A | 6/1980 | Giurtino |
| 4,239,041 A | 12/1980 | Popovich et al. |
| 4,311,587 A | 1/1982 | Nose et al. |
| 4,470,429 A | 9/1984 | Johnson |
| 4,566,480 A | 1/1986 | Parham |
| 4,593,717 A * | 6/1986 | Levasseur ................ 137/556.6 |
| 4,821,996 A | 4/1989 | Peluso et al. |
| 4,904,245 A | 2/1990 | Chen et al. |
| 4,950,230 A | 8/1990 | Kendell |
| 4,982,760 A | 1/1991 | Mustaklem |
| 5,104,387 A | 4/1992 | Pokorney et al. |
| 5,135,026 A | 8/1992 | Manska |
| 5,439,452 A | 8/1995 | McCarty |
| 5,443,453 A | 8/1995 | Walker et al. |
| 5,540,668 A | 7/1996 | Wilson, Jr. et al. |
| 5,713,850 A | 2/1998 | Heilmann et al. |
| 5,832,959 A | 11/1998 | Szymczakowski et al. |
| 5,839,470 A | 11/1998 | Hiejima et al. |
| 6,135,153 A | 10/2000 | Cleland, Sr. et al. |

FOREIGN PATENT DOCUMENTS

| | | |
|---|---|---|
| EP | 0 354 915 B1 | 12/1994 |
| EP | 0 715 860 B1 | 6/1996 |
| EP | 0 768 099 A1 | 4/1997 |
| EP | 0 800 837 A2 | 10/1997 |
| EP | 1 106 191 | 6/2001 |
| WO | WO 88/06895 | 9/1988 |
| WO | WO 96/22118 | 7/1996 |
| WO | WO 2004/022151 A1 | 3/2004 |

* cited by examiner

MULTIWAY VALVE

CROSS REFERENCE TO RELATED APPLICATIONS

This application is an national phase application based on PCT/IB2003/003166, filed Aug. 5, 2003, the content of which is incorporated herein by reference, and claims the right to priority based on Italian Application No. MI2002A001895, filed Sep. 6, 2002.

BACKGROUND OF THE INVENTION

The present invention relates to a flow shut-off element.

In particular, the flow shut-off element according to the present invention is intended for applications in the medical field and, in greater detail, this device can be used in circuits for peritoneal dialysis.

As is known, a circuit for peritoneal dialysis consists of at least one tube connected to the patient's peritoneal cavity; in practice, the tube consists of a surgically implanted fixed catheter having an outlet inside the peritoneal cavity, and a portion outside the body to which is connected a further length of tubing designed to be replaced periodically.

The circuit thus has a first infusion line connected to one or more bags containing fresh fluid for introduction into the patient's peritoneal cavity and a second drainage line for the waste fluid, designed to carry the fluid located in the patient's peritoneal cavity to one or more bags for subsequent disposal.

In particular, the infusion and drain lines are joined by a Y-connector to a third line in communication with the fixed catheter and consequently with the peritoneal cavity.

Briefly, in a peritoneal dialysis operation the dialysis fluid which has remained for the necessary time in the patient's peritoneal cavity has to be drained off and sent to the collection bags for disposal, and the Y-connector then has to be flushed through by passing fresh fluid from the infusion line to the drain line, after which, in a final stage of infusion, a fresh fluid has to be introduced into the patient's peritoneal cavity.

Consequently, in order to carry out the aforesaid operations, it is necessary to use shut-off elements capable of operating in the area of the junction between the various tubes to ensure the correct flow of the fluids.

A first known technique requires the use of clamps (at least one for each tube), which are operated manually, thus mechanically deforming the tubing to the point at which its cross section is completely closed.

In particular, for carrying out the aforesaid operations, the infusion line is first closed to allow the fluid to pass from the patient towards the disposable bags; secondly the tubing leading towards the peritoneal cavity is closed, enabling the connection area to be washed by passing fresh fluid towards the disposable fluid bag, after which the drain line is closed, thus allowing fresh fluid to be introduced into the peritoneal cavity.

Clearly, since manual opening and closing operations have to be performed on the tubing, a degree of experience and attention is required from the user who might otherwise make mistakes in the sequence of stages, or even carry out incorrect operations which could result in serious harm to the patient's health.

A further known technique according to Patent no. EP 768099 requires the use of a stopcock consisting of a valve body on which three channels for the passage of fluids converge.

The valve body has a central cavity which communicates with the aforesaid channels, and which is designed to receive a projecting portion of a movable selector.

The rotation of the selector creates different paths for the fluid within the stopcock, these paths being created simply by the angular position of the said selector.

This stopcock is also provided with suitable projections located within the cavity formed by the valve body, and with corresponding notches formed on a cylindrical portion of the said selector.

In practice, the function of these elements is to signal to the user that the correct angular positions of the selector have been reached, these positions providing an optimal predetermined passage of fluid within the stopcock.

However, the known technique summarized above has certain drawbacks and/or operational limitations.

In the first place, the valves of the known type described above have no versatility at all, and are difficult to adapt.

If these devices were to be modified and/or adapted in any way, it would be necessary to replace most parts, if not all, of the stopcock.

Furthermore, with the aforementioned shut-off element it is not possible to specify the sequence of successive operations which the valve is to perform; in particular, the operator only has the sensation of correct positioning in the various operating conditions, but there is no indication as to the correctness of the valve opening/closing sequence being executed by the device.

SUMMARY OF THE INVENTION

The object of the present invention is therefore essentially to overcome the aforesaid drawbacks.

A first object of the invention is to provide a flow shut-off element which is as versatile and adaptable as possible.

A further object of the invention is to maintain maximum reliability of the device without essentially detracting from the intrinsic simplicity of construction of the known devices, and while also keeping the costs low, in view of the fact that the valves to which the invention relates are generally of the disposable type.

A subsidiary object of the invention is to provide a shut-off element in which the correct sequence of operations is made compulsory, in such a way that a user cannot inadvertently carry out these operations in an incorrect temporal sequence.

Finally, a further object is to prevent the re-use of these valves when they have already been used.

These and other objects which will be made clear in the course of the description are essentially achieved by a flow shut-off element according to the present claims.

BRIEF DESCRIPTION OF THE DRAWINGS

Further characteristics and advantages will be made clear by the following detailed description of a preferred, but not exclusive, embodiment of a flow shut-off element according to the illustrations in the attached drawings, in which.

DETAILED DESCRIPTION

With reference to the aforesaid figures, the number 1 indicates the whole of a flow shut-off element for use, in particular, in medical applications, and more particularly in circuits for peritoneal dialysis.

Figure 14:
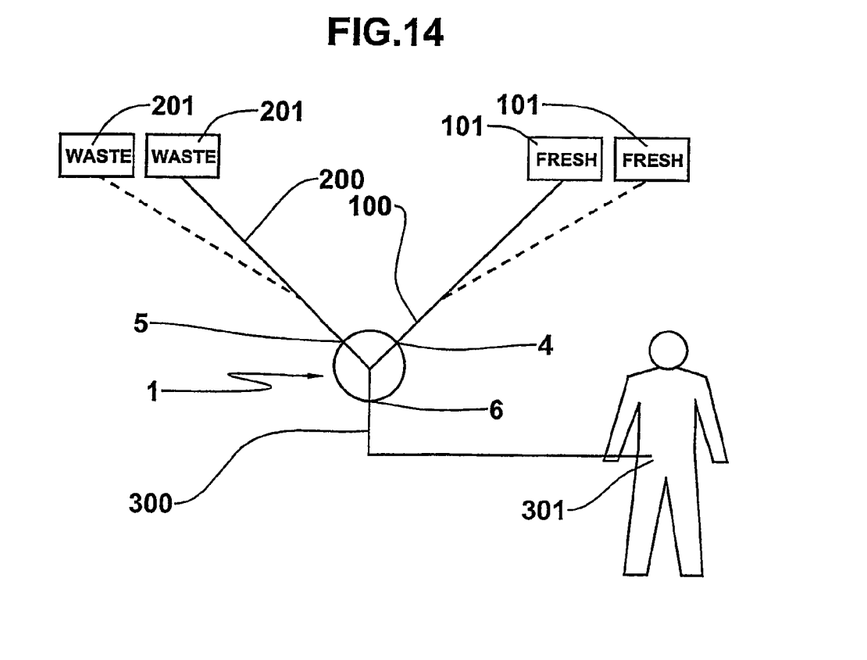
FIG. 14 shows in a schematic way a circuit for peritoneal dialysis.

As shown in FIG. 14, the shut-off element 1 is designed to operate (as explained more fully below) in the area of the junction of the infusion line 100 and the drain line 200 with the inlet line 300 leading to the patient's peritoneal cavity.

To provide greater structural detail, it can be seen that the shut-off element consists of a valve body 2 (see FIGS. 1 to 4) which has an essentially discoid profile and has a plurality of accesses 4, 5 and 6, of which there are three in this particular case, designed to be connected, respectively, to the infusion line 100, to the drain line 200, and to the patient line 300.

In particular, the terminal portions of the tubes forming the aforementioned lines are engaged with the projecting portions of these accesses and the connection is secured by the friction generated between the material forming the tubes and the material, for example polycarbonate, from which the valve body is made.

The accesses 4, 5 and 6 thus form three channels which can put the infusion line 100, drain line 200 and patient line 300 directly into fluid communication with an inner cavity 3 of the valve body 2.

The flow shut-off element 1 also comprises a selector 7 (see FIGS. 8 to 12) also of essentially discoid shape, which can be associated with the valve body 2 and is movable relatively to the latter into a predetermined number of operating positions in which it forms, by interacting with the said valve body, predetermined paths in which the flow of the fluid is permitted and/or shut off between the said accesses 4, 5 and 6.

In particular, the selector, made for example from polyethylene by injection moulding, is provided with a projecting portion 13 which has an essentially cylindrical profile and is at least partially shaped in a complementary way to the inner cavity 3 of the valve body 2.

It should be noted that the portion 13 can alternatively have a conical shape (obviously with a small degree of taper), in order to improve the fluidtightness between the said portion 13 and the cavity 3.

In particular, in operating conditions, the selector 7 is mounted on the valve body 2 in such a way that the projecting portion 13 is inserted into the cavity 3 in a fluidtight way.

The projecting portion 13 has a cross section (shown in FIG. 11) in which can be seen channels 16 designed to interact with the accesses 4, 5 and 6 formed in the valve body 2 in order to create various paths for the fluid within the shut-off element, according to the relative angular positions of the selector 7 and the valve body 2.

In detail, the first, second and third accesses 3, 4 and 5 are brought into fluid communication in a predetermined sequence by relative rotations of the selector about the axis of rotation 15.

According to the peritoneal dialysis procedure, the selector 7 must be capable of switching the shut-off element at least between a condition in which the flow of fluid is prevented; a condition in which fluid passes from the third to the second access 6, 5, in which the fluid is allowed to drain from the patient's peritoneal cavity 301 to the waste bags 201; a condition in which fluid passes from the first to the second access 4, 5, in which the connector is washed by making fresh fluid pass towards the waste bag 201; and a condition in which fluid passes from the first to the third access 4, 6, in which fresh fluid can be infused from the bags 101 into the patient's peritoneal cavity 301. The configuration of the channels 16 and the arrangement of the accesses 4, 5 and 6 is such that a rotation of the selector from an initial position in the direction of the arrow 23 shown in FIG. 8 makes it possible to pass in succession from the fluid flow shut-off condition to the drain condition, to the washing condition and then to the infusion condition, finally reaching a condition in which the passage of fluid is stopped within the shut-off element.

Advantageously, the shut-off element according to the present invention also comprises an auxiliary element 8 shown in FIGS. 5, 6, 7 and 13, which also has an essentially discoid shape and is designed to be removably associated with the valve body 2.

In this context it should be noted that the valve body 2 is provided with one or preferably numerous locating blocks 25, which, more precisely, consist of small catches projecting from the channels 4, 5 and 6 (see FIG. 1); these locating blocks enable the auxiliary element 8 to be positioned correctly on the said valve body.

Figure 7:
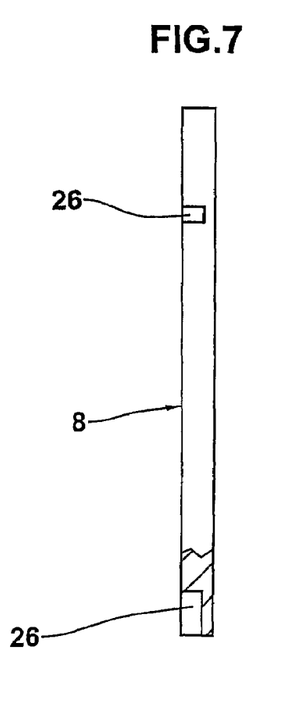
FIG. 7 shows a lateral view in partial section of the auxiliary element of FIG. 5.

As can be seen in FIG. 7, the auxiliary element 8 has corresponding notchs 26 designed to receive the said locating blocks 25 of the valve body 2.

During assembly, the auxiliary element 8 is positioned to bear on the valve body 2 and then the projecting portion 13 of the selector is inserted into the cavity 3 of the valve body where it is engaged by a snap fit.

It should also be noted that the valve body has an inner perimetric wall 21 delimiting the inner cavity 3.

In a corresponding way, the auxiliary element 8 has a central through cavity 24, through which an upper portion 21a of the perimetric wall 21 passes during assembly.

The selector 7 is also provided with a circular ring 7a which is coaxial with the projecting portion 13 and interacts with this portion to delimit a cavity 14 for engagement with the valve body 2.

In other words, the upper portion 21a of the perimetric wall 21 is designed to be inserted and guided in its movement by the engagement cavity 14 of the said selector into a condition in which the various components are engaged.

Figure 1:
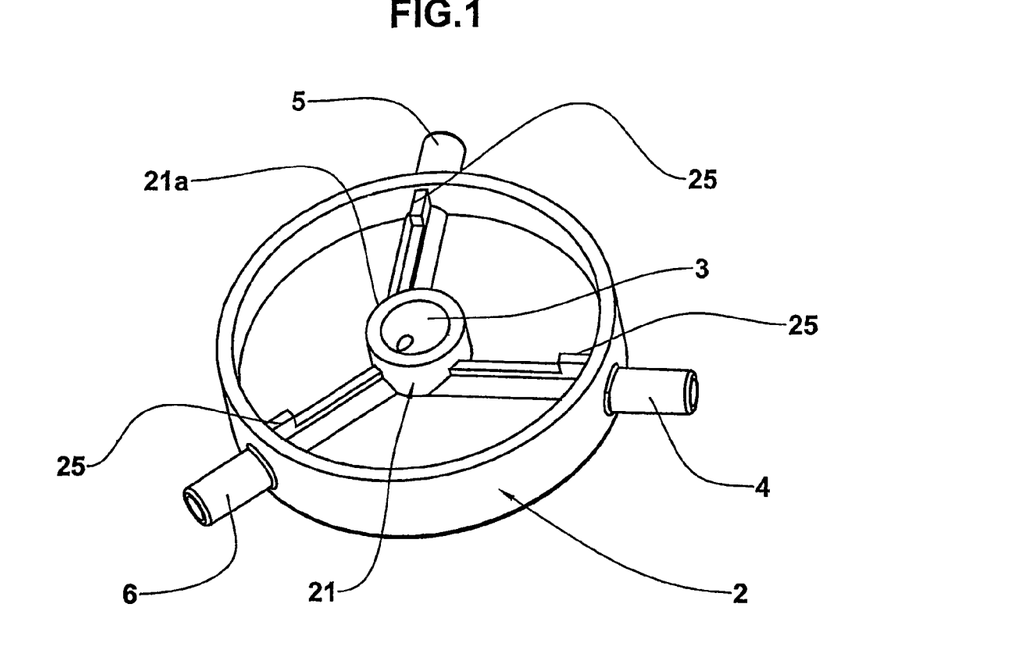
FIG. 1 shows a perspective view of a valve body according to the present invention.
Figure 2:
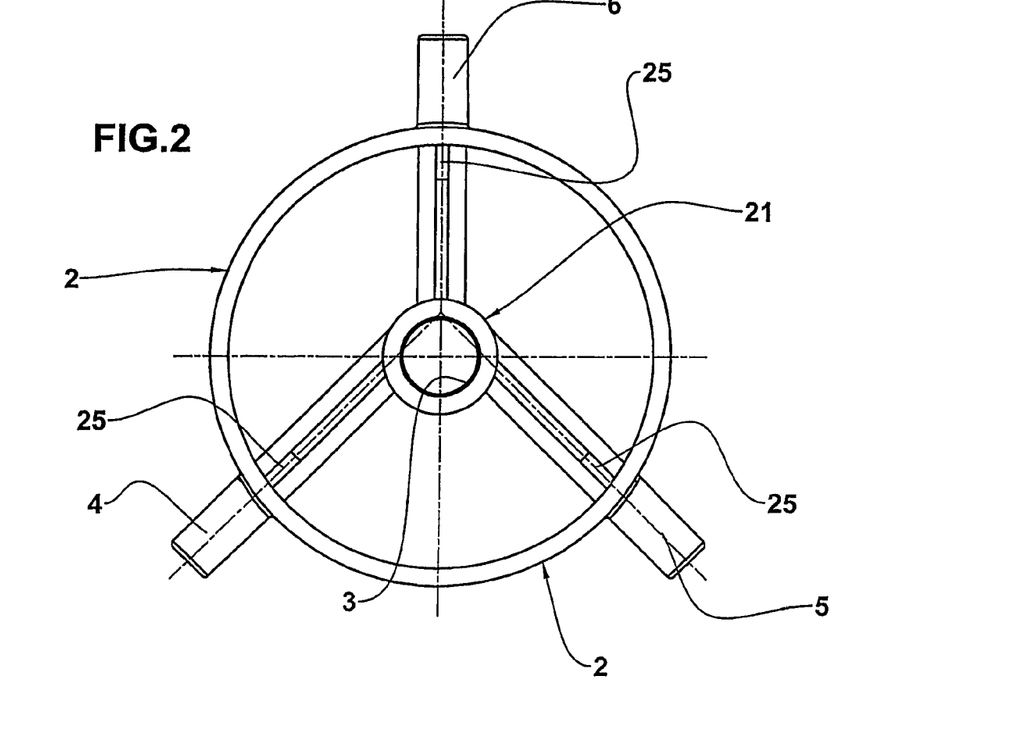
FIG. 2 shows a view from above of the body of FIG. 1.
Figure 3:
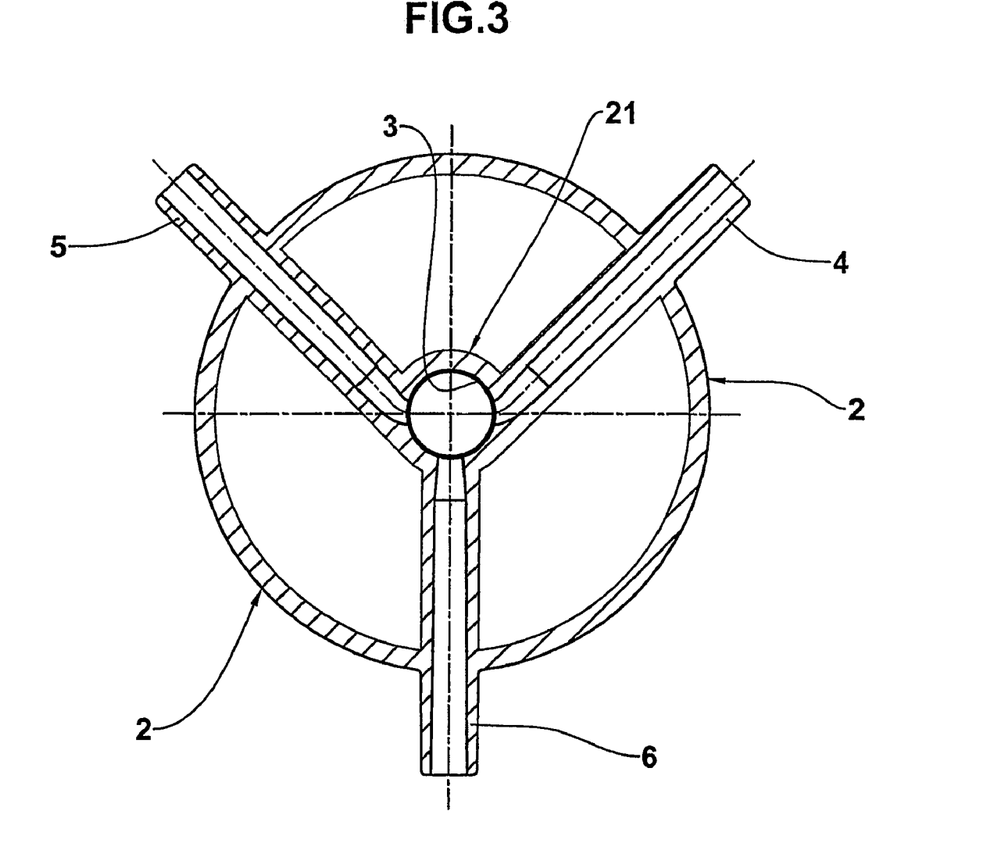
FIG. 3 shows a transverse section through the valve body shown in FIG. 1.
Figure 4:
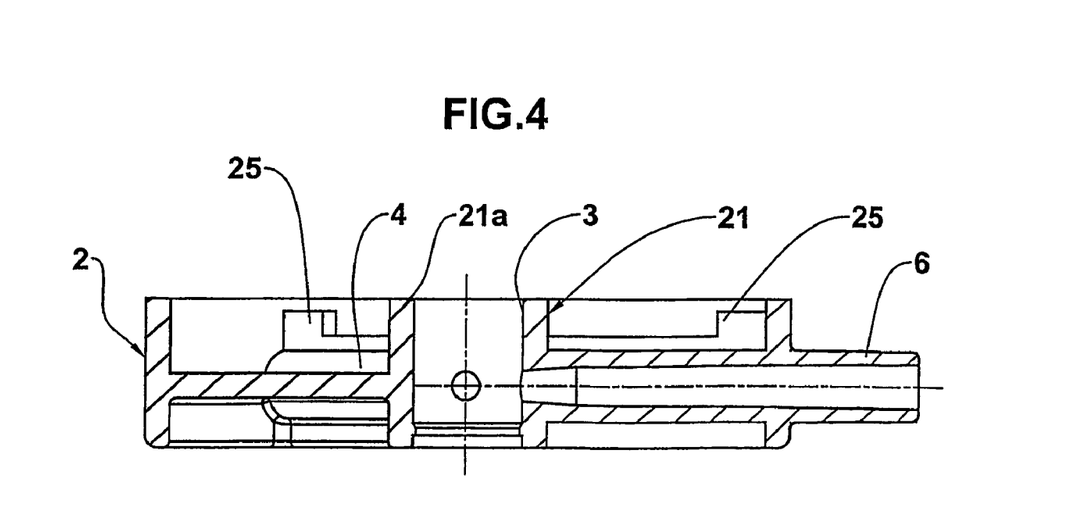
FIG. 4 shows a longitudinal section through the valve body shown in FIG. 1.
Figure 5:
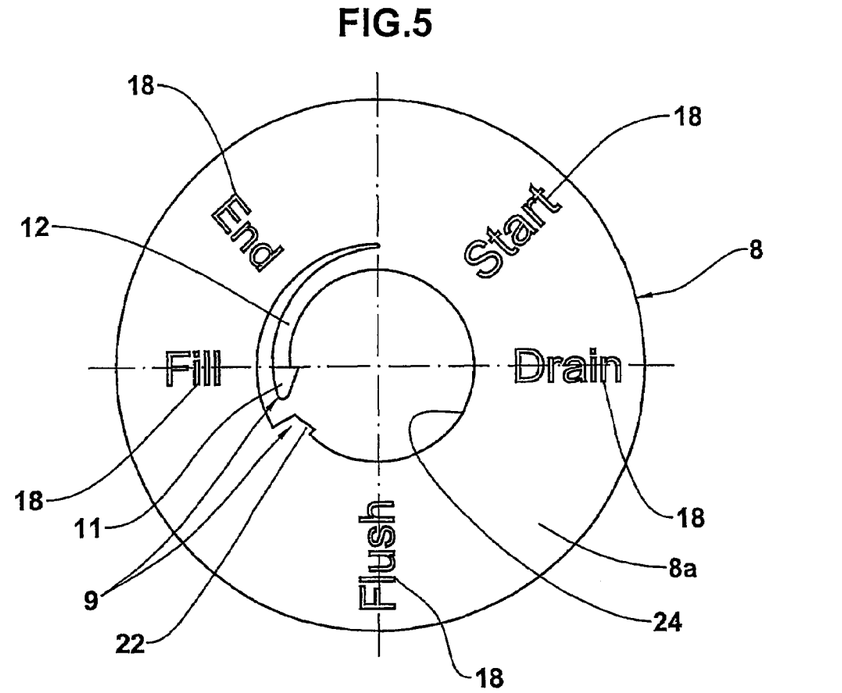
FIG. 5 shows an auxiliary element which can be associated with the valve body shown in FIG. 1.

Turning now to the illustration in FIG. 5, it can be seen that the auxiliary element 8 is provided with positioning means 9 for determining when one of the predetermined operating positions of the selector is reached.

In particular, the selector 7 can comprise a predetermined number of catches and/or notches 10 (a plurality of notches being provided in the illustrated embodiment), while the positioning means 9 can have at least one corresponding catch or notch 11 (in the present case, a single locking catch is provided) designed to engage in at least one of the said catches and/or notches 10.

The positioning means 9 consist, in particular, of an elastic element 12 which extends along a curved axis from the main body of the auxiliary element 8 and has the locking catch 11 at its free end. This catch 11 interacts, in particular, with the notches 10 of the selector 7, which are formed on the aforesaid circular ring 7a. In particular, following a rotation of the selector 7, the configuration of the notches 10 and the catch 11 is such that the elastic element 12 is deformed in a radial direction until the catch 11 snaps into an angularly successive notch 10.

Figure 8:
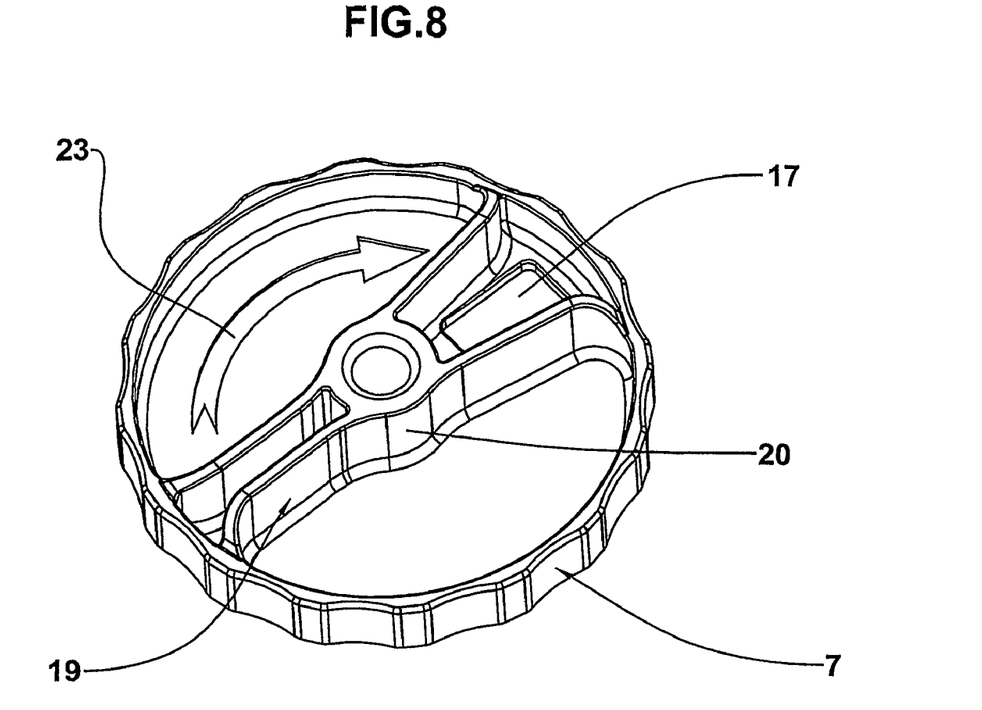
FIG. 8 shows in a perspective view from above a selector which can be associated with the valve body shown in FIG. 1.

The particular configuration of the catch 11 and the notches 10 is such that the selector 7 can rotate with respect to the valve body 2 only in the direction indicated by the number 23 in FIG. 8.

Figure 9:
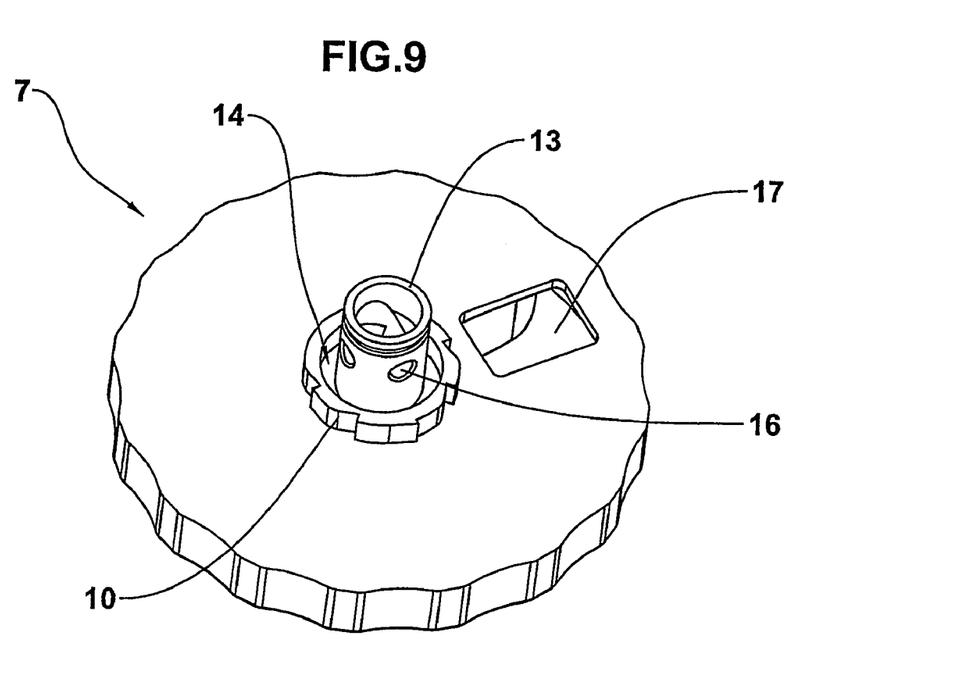
FIG. 9 shows in a perspective view from below the selector shown in FIG. 8.
Figure 10:
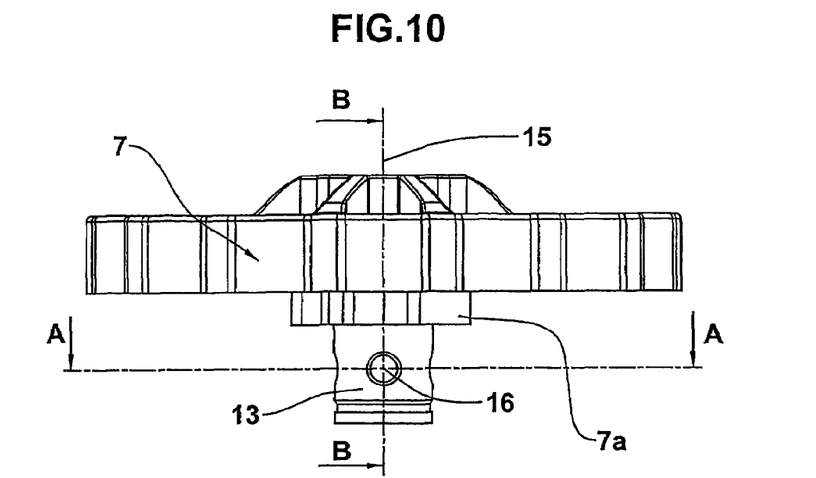
FIG. 10 shows in a lateral view the selector shown in FIG. 8.
Figure 11:
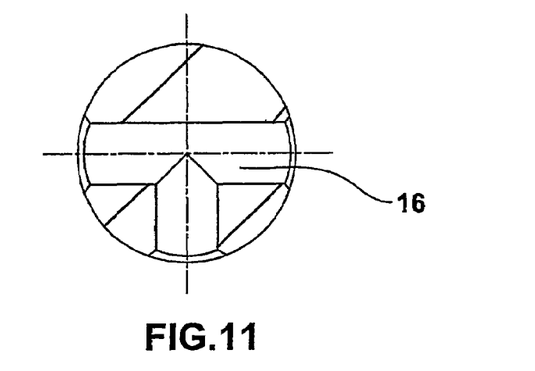
FIG. 11 shows a section taken through the line A-A of the selector of FIG. 10.
Figure 12:
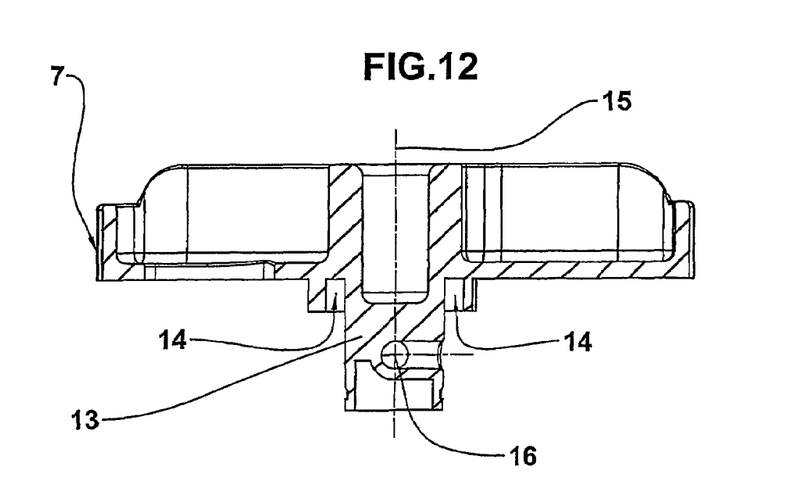
FIG. 12 shows a transverse section taken through the line B-B of the selector of FIG. 10.

Rotation in the opposite direction is prevented by the undercut of the catch 11 which bears on the corresponding undercuts formed in the circular ring of the selector (see, in particular, FIG. 9).

Figure 6:
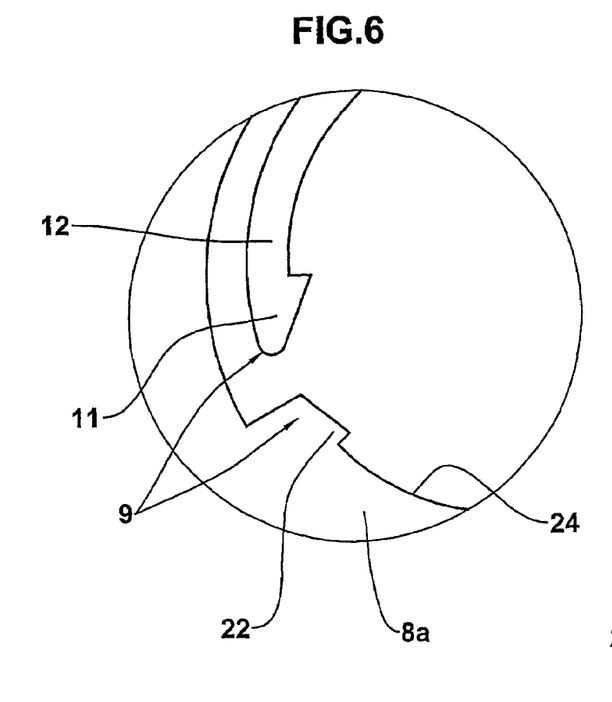
FIG. 6 shows a detail of the positioning means of the auxiliary element of FIG. 5.

It can be seen in FIG. 6 that the positioning means 9 also comprise a stop projection 22 which can form a mechanical stop to the rotary movement of the selector 7.

In particular, the function of the stop projection 22 is to delimit the end of travel of the selector 7.

In other words, when the valve body 2, the auxiliary element 8 and the selector 7 have been assembled together in the correct initial position, it is possible to make successive rotations of the selector in the direction indicated by the arrow 23 of FIG. 8 into the various operating conditions of the shut-off element.

The reaching of the various stages of operation is indicated by the snap-fitting of the catch 11 into the corresponding notches 10, and, when all the operating positions have been passed through in sequence, the stop projection 22 interacts with the said notches 10 and thus prevents further rotation in the direction of the arrow indicated by the reference 23.

At the same time, the catch 11 inserted into another corresponding notch 10 prevents movement in the reverse direction, thus effectively preventing the re-use of the shut-off element.

Finally, it should be noted that the selector 7 has at least one aperture 17 for permitting views of corresponding areas of the underlying auxiliary element.

Thus different positions of the selector 7 relative to the valve body 2 enable different portions of the upper surface 8a of the auxiliary element 8 to be viewed.

Figure 13:
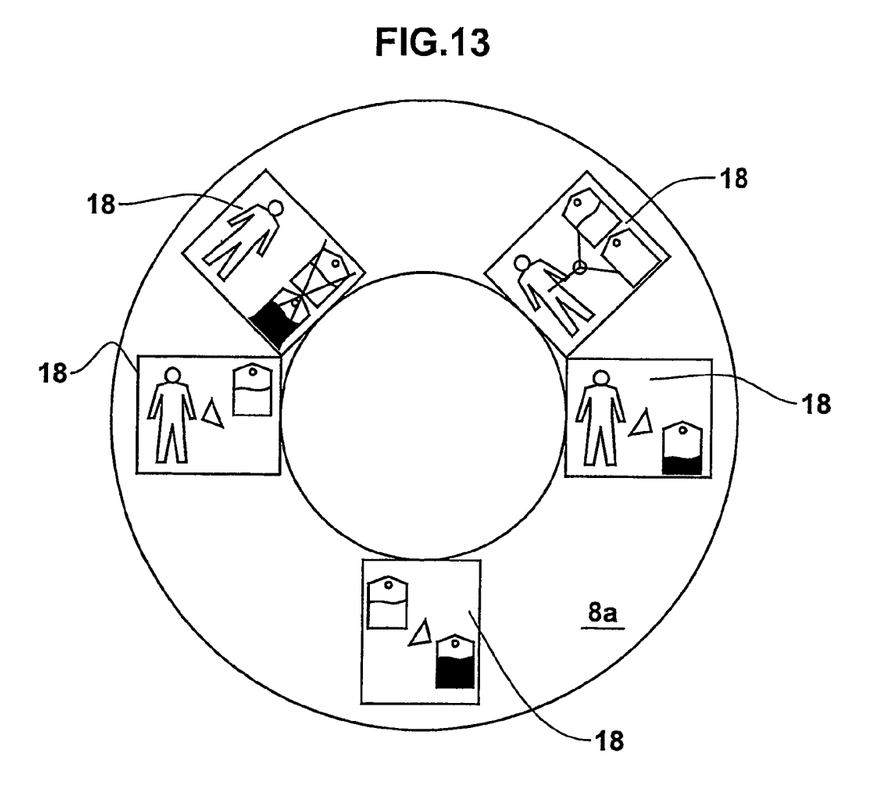
FIG. 13 shows in a schematic way a variant of the auxiliary element of FIG. 5.

This upper surface 8a has, in particular, predetermined visual representations 18 illustrated by way of example in FIGS. 5 and 13.

The representations 18 can be, in particular, graphic symbols and/or alphanumeric indications and/or colours relating to the paths in which the fluid flow is permitted and/or shut off between the said accesses.

With reference to the screen-printed auxiliary element shown in FIG. 5, it can be seen that, in the initial assembly position, the aperture 17 is located over the wording "START"; a first rotation in the direction of the arrow 23 places the aperture over the wording "DRAIN" and at the same time the shut-off element moves from a condition in which no flow of fluid is permitted within the cavity 3 to a condition in which the fluid is allowed to drain from the patient's peritoneal cavity 310 to the waste bags 201.

A further rotation of the selector 7 places the aperture 17 over the wording "FLUSH", where the shut-off element is in the flushing condition, allowing fresh fluid to flow towards the waste bags 201.

A further rotation places the aperture 17 over the wording "FILL" and the configuration of the shut-off element is such that fresh fluid is allowed to flow towards the patient's peritoneal cavity 301.

A further rotation in the clockwise direction then places the aperture over the wording "END" in which no flow of fluid is permitted within the shut-off element.

In this final condition, it is no longer possible to carry out any rotation in either the clockwise or the anti-clockwise direction, and the said shut-off element therefore has to be removed.

Finally, as shown in FIG. 8, the selector 7 has a grip portion 19 to enable the operator to rotate it with respect to the valve body 2; the grip portion 19 is, in particular, formed by suitable stiffening ribs 20 which extend transversely with respect to the axis of rotation 15.

The invention yields considerable advantages.

In the first place, the presence of an auxiliary body, which carries the screen-printed wording relating to the operations which the shut-off element is executing and also carries the positioning means which provide an active indication of the reaching of the correct position, imparts a greater versatility to the device.

This is because the shut-off element can be adapted simply by replacing the auxiliary disc in such a way that the wording and/or graphic representations appearing on it can be modified.

Additionally, a modification of the positioning means of this auxiliary element makes it possible to carry out larger or smaller relative rotations and to stop the shut-off element in different angular positions.

These advantages are achieved without essentially affecting the simplicity of construction and the production costs of the shut-off element, which has to be replaced after every use.

Furthermore, the particular configuration of the positioning means and of the corresponding notches present on the selector make it possible to specify a single direction of rotation and therefore a sequence of the possible operations to be executed, with no possibility of any error by the operator.

The invention claimed is:

1. A flow shut-off element comprising:
   a valve body having an inner cavity and a plurality of accesses communicating with said inner cavity configured to allow a flow of fluid, said valve body having an inner perimetric wall forming said inner cavity;
   a selector movable relative to said valve body into a predetermined number of operating positions, said selector being active in said inner cavity to form, as a result of movements into said operating positions, predetermined paths in which the fluid flow is permitted or shut off between said accesses, said selector comprising a projecting portion configured to be inserted, in operating conditions, into the inner cavity of said valve body, relative movements of said selector with respect to said valve body causing different operating positions to be reached, said projecting portion being inserted in a fluid-tight way into the inner cavity of the valve body; said selector having at least one aperture; said selector having a circular ring essentially coaxial with said projecting portion;
   an auxiliary element associated with said valve body and made in the form of an independent body, said auxiliary element being essentially discoid in shape and having a central through cavity, said inner perimetric wall passing through said central through cavity, said auxiliary element having a surface facing said selector, said surface having predetermined visual representations, said representations including at least one of graphic symbols, alphanumeric indications, or cobra relating to the paths in which the fluid flow is shut off or permitted between said accesses, wherein different relative positions of mid selector with respect to said valve body provide visual access through said aperture to corresponding visual representations of said surface; and positioning means configured to enable an operator to determine when one of said predetermined operating positions of said selector has been reached, wherein reaching one of mid predetermined operating positions is indicated by a snap fitting of a catch into a corresponding notch, said positioning means being configured to permit a relative rotation of said selector with respect to said valve body in only one direction; said positioning means being arranged in said central through cavity; and said positioning means being operative between said auxiliary element and said circular ring.

2. The flow shut-off element of claim 1, wherein said positioning means includes a predetermined number of catches or notches located on said circular ring and at least one corresponding catch or notch located on said auxiliary element, said at least one corresponding catch or notch on the auxiliary element being configured to be engaged in at least one of said predetermined number of notches or catches of the circular ring, to perceive when said predetermined operating positions of said selector have been reached.

3. The flow shut-off element of claim 1, wherein said positioning means includes an elastic element having a locking catch, said elastic element being located on said auxiliary element, said locking catch being designed to interact with corresponding notches present in said circular ring.

4. The flow shut-off element of claim 3, wherein said locking catch is positioned at a free end of said elastic element.

5. The flow shut-off element of claim 3, wherein said elastic element has an essentially curved axis of extension.

6. The flow shut-off element of claim 1, wherein said circular ring and said projecting portion defines an engagement cavity for receiving said valve body.

7. The flow shut-off element of claim 6, wherein an upper portion of said perimetric wall is inserted and guided in its movement by said engagement cavity.

8. The flow shut-off element of claim 1, wherein said positioning means comprise a stop projection to form a mechanical stop to the movement of said selector.

9. The flow shut-off element of claim 1, wherein said positioning means comprise an elastic element having a locking catch, said elastic element being located on said auxiliary element, said locking catch being designed to interact with corresponding notches present in said circular ring; said positioning means comprising a stop projection to form a mechanical stop to the movement of said selector; said locking catch and said stop projection projecting radially towards a center of said central through cavity of said auxiliary element.

10. The flow shut-off element of claim 1, wherein said projecting portion of said selector has an essentially cylindrical shape and is at least partially shaped to be complementary to said inner cavity of said valve body.

11. The flow shut-off element of claim 1, wherein said selector is movable with respect to said valve body about an axis of rotation, said projecting portion having an axis of extension coinciding with the axis of rotation.

12. The flow shut-off element of claim 1, wherein said projecting portion includes predetermined channels configured to interact with said accesses formed in said valve body to create different fluid paths within said flow shut-off element according to the relative positions of said selector with respect to said valve body.

13. The flow shut-off element of claim 1, wherein said valve body includes at least a first, a second, and a third access for the fluid, said selector being capable of switching between a condition in which the flow of fluid is prevented, a condition in which fluid flows from the third access to the second access, a condition in which fluid flows from the first access to the second access, and a condition in which fluid flows from the first access to the third access.

14. The flow shut-off element of claim 1, wherein said selector has a grip portion to enable a user to rotate it with respect to said valve body.

15. The flow shut-off element of claim 14, wherein said grip portion is delimited by stiffening ribs extending transversely with respect to an axis of rotation.

16. The flow shut-off element of claim 1, wherein at least one of said selector or said valve body are essentially discoid in shape.

17. The flow shut-off element of claim 1, wherein said valve body has at least one locating block to enable the auxiliary element to be positioned correctly on said valve body.

18. The flow shut-off element of claim 17, wherein said auxiliary element has corresponding notches configured to receive said at least one locating block of the valve body.

19. The flow shut-off element of claim 1, wherein said auxiliary element is removably associated with said valve body.

* * * * *

UNITED STATES PATENT AND TRADEMARK OFFICE
CERTIFICATE OF CORRECTION

PATENT NO. : 7,469,716 B2
APPLICATION NO. : 10/525728
DATED : December 30, 2008
INVENTOR(S) : Andrea Parrino et al.

Page 1 of 1

It is certified that error appears in the above-identified patent and that said Letters Patent is hereby corrected as shown below:

In claim 1, column 7, line 6, "cobra" should read --colors--.

In claim 1, column 7, line 8, "mid" should read --said--.

In claim 1, column 7, lines 15, "mid" should read --said--.

Signed and Sealed this

Twenty-fourth Day of February, 2009

JOHN DOLL
*Acting Director of the United States Patent and Trademark Office*